United States Patent
Maeda et al.

(10) Patent No.: US 12,195,957 B2
(45) Date of Patent: Jan. 14, 2025

(54) CLEANING DEVICE, CLEANING SYSTEM INCLUDING SAME, AND CLEANING METHOD USING SAID CLEANING DEVICE

(71) Applicant: PANASONIC INTELLECTUAL PROPERTY MANAGEMENT CO., LTD., Osaka (JP)

(72) Inventors: Yasunari Maeda, Osaka fu (JP); Naoki Shibata, Osaka fu (JP); Sakiho Asa, Nara ken (JP); Mai Saito, Osaka fu (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 135 days.

(21) Appl. No.: 17/616,574

(22) PCT Filed: May 28, 2020

(86) PCT No.: PCT/JP2020/021038
§ 371 (c)(1),
(2) Date: Dec. 3, 2021

(87) PCT Pub. No.: WO2020/261865
PCT Pub. Date: Dec. 30, 2020

(65) Prior Publication Data
US 2022/0251816 A1    Aug. 11, 2022

(30) Foreign Application Priority Data
Jun. 27, 2019    (JP) .................. 2019-119723

(51) Int. Cl.
*E03D 9/02*    (2006.01)
*A61L 2/18*    (2006.01)
(Continued)

(52) U.S. Cl.
CPC ............. *E03D 9/02* (2013.01); *A61L 2/183* (2013.01); *A61L 2/26* (2013.01); *B01F 23/232* (2022.01);
(Continued)

(58) Field of Classification Search
CPC ...... C02F 1/4672; C02F 2307/12; C02F 1/78; C02F 2201/005; B08B 3/08; B08B 3/10;
(Continued)

(56) References Cited

U.S. PATENT DOCUMENTS 4,467,480 A * 8/1984 Keller .................... E03D 9/037
4/225.1
5,745,928 A * 5/1998 Armanno, Sr. ......... E03D 9/037
4/225.1
(Continued)

FOREIGN PATENT DOCUMENTS

CN         108474200          8/2018
EP         1431249 A1 *       6/2004     ............ B64D 11/02
(Continued)

OTHER PUBLICATIONS

Extended European Search Report issued in EP Application No. 20831163.9, dated Jul. 22, 2022.
(Continued)

*Primary Examiner* — Benjamin L Osterhout
(74) *Attorney, Agent, or Firm* — GREENBLUM & BERNSTEIN, P.L.C.

(57) ABSTRACT

A cleaning device including a disinfection water supply portion to supply cleaning water with a dissolved disinfection component, and a bubble generation portion to contain bubbles into the cleaning water on a downstream side of the disinfection water supply portion.

18 Claims, 5 Drawing Sheets

(51) Int. Cl.
  *A61L 2/26*    (2006.01)
  *B01F 23/232*  (2022.01)
  *B08B 3/08*    (2006.01)
  *B08B 9/032*   (2006.01)
  *C02F 1/467*   (2023.01)
  *B01F 101/24*  (2022.01)
  *B08B 3/10*    (2006.01)
  *C02F 1/78*    (2023.01)
  *E03C 1/046*   (2006.01)
  *E03D 9/00*    (2006.01)
  *E03D 13/00*   (2006.01)

(52) U.S. Cl.
  CPC .............. *B08B 3/08* (2013.01); *B08B 9/032* (2013.01); *C02F 1/4672* (2013.01); *A61L 2202/11* (2013.01); *A61L 2202/17* (2013.01); *B01F 2101/24* (2022.01); *B08B 3/10* (2013.01); *B08B 2203/005* (2013.01); *B08B 2209/032* (2013.01); *C02F 1/78* (2013.01); *C02F 2201/005* (2013.01); *C02F 2307/12* (2013.01); *E03C 1/046* (2013.01); *E03D 9/005* (2013.01); *E03D 13/00* (2013.01)

(58) Field of Classification Search
  CPC ............ B08B 9/032; B08B 2209/032; B08B 2203/005; E03D 9/02; E03D 9/005; E03D 13/00; A61L 2/26; A61L 2/183; A61L 2202/17; A61L 2202/11; B01F 23/232; B01F 2101/24; E03C 1/046
  See application file for complete search history.

(56) References Cited

U.S. PATENT DOCUMENTS

| | | | | |
|---|---|---|---|---|
| 6,000,067 A * | 12/1999 | Cascia | .................... | B60R 15/04 4/223 |
| 8,099,802 B2 * | 1/2012 | Yamaguchi | ............. | E03D 11/08 4/300 |
| 8,156,608 B2 * | 4/2012 | Field | ......................... | B08B 3/02 15/319 |
| 9,714,507 B1 * | 7/2017 | Snell | ....................... | E03D 9/005 |
| 2007/0186368 A1 | 8/2007 | Field et al. | | |
| 2010/0146693 A1 * | 6/2010 | Yamaguchi | ................ | E03D 5/10 4/420 |
| 2011/0072570 A1 * | 3/2011 | Morotomi | .................. | E03D 9/08 4/420.4 |
| 2015/0013058 A1 * | 1/2015 | Bucher | .................... | E03D 9/037 4/224 |
| 2015/0183660 A1 * | 7/2015 | Wright | ................ | B01D 21/2433 210/801 |
| 2017/0275865 A1 * | 9/2017 | Hashimoto | ............... | E03D 9/08 |
| 2017/0275866 A1 * | 9/2017 | Hashimoto | ............... | E03D 9/08 |
| 2017/0275867 A1 * | 9/2017 | Hashimoto | ............... | E03D 9/08 |

FOREIGN PATENT DOCUMENTS

| | | |
|---|---|---|
| EP | 3 677 731 | 7/2020 |
| JP | 2000-248601 | 9/2000 |
| JP | 2011-088979 | 5/2011 |
| JP | 2011-256708 | 12/2011 |
| JP | 2017-066636 | 4/2017 |
| JP | 2018-025061 | 2/2018 |
| JP | 2019-039267 | 3/2019 |
| JP | 2019-065492 | 4/2019 |

OTHER PUBLICATIONS

Official Communication issued in International Patent Application No. PCT/JP2020/021038, dated Aug. 18, 2020, along with an English translation thereof.

China Official Action received in CN Application No. 202080033791.1, dated Nov. 14, 2022.

Search Report accompanying China Official Action received in CN Application No. 202080033791.1, dated Nov. 14, 2022.

* cited by examiner

CLEANING DEVICE, CLEANING SYSTEM INCLUDING SAME, AND CLEANING METHOD USING SAID CLEANING DEVICE

TECHNICAL FIELD

The disclosure relates to a cleaning device, a cleaning system provided with the cleaning device and a cleaning method using the cleaning device.

BACKGROUND ART

Conventionally known is a cleaning device to supply cleaning water for cleaning various kinds of cleaning targets.

For example, the following Patent Literature 1 discloses a toilet cleaning system having a gas-liquid mixing portion and an air introduction portion to introduce gas containing functional gas such as ozone gas into the gas-liquid mixing portion, and the toilet cleaning system is provided with a bubble mixing portion to make air into bubbles to be mixed in a cleaning water.

CITATION LIST

Patent Literature

PTL 1: Japanese Unexamined Patent Application Publication No. 2019-39267

SUMMARY

Technical Problem

In the toilet cleaning system disclosed in the above-mentioned Patent Literature 1, the bubbles contained in cleaning water include ozone gas; however, ozone gas is hardly dissolved in cleaning water itself, therefore, further improvement is expected.

The present invention is achieved in view of the above-mentioned problems and has an object to provide a cleaning device capable of improving disinfection ability of cleaning water, a cleaning system having the cleaning device, and a cleaning method using the cleaning device.

Solution to Problem

In order to achieve the above-mentioned object, the cleaning device of one embodiment of the present invention includes a disinfection water supply portion to supply cleaning water with a dissolved disinfection component, and a bubble generation portion to contain bubbles into the cleaning water on a downstream side of the disinfection water supply portion.

In order to achieve the above-mentioned object, in the cleaning system including the cleaning device of one embodiment of the present invention, a downstream side of the bubble generation portion is connected to at least one of a water supply channel to supply cleaning water to a toilet and a water discharge channel connected to a water discharge portion of the toilet.

In order to achieve the above-mentioned object, in the cleaning method for cleaning a cleaning target using the cleaning device of one embodiment of the present invention, cleaning water is supplied to the cleaning target each time a predetermined fixed time elapses.

Advantageous Effects of Invention

The cleaning device and the cleaning system provided with the cleaning device according to the embodiments of the present invention are constituted as mentioned above and improve the disinfection ability using of cleaning water. In the cleaning method according to the embodiments of the present invention, the cleaning target is effectively cleaned.

DESCRIPTION OF EMBODIMENTS

The embodiments of the present invention are explained based on the drawings.

In the following embodiments, directions such as the vertical direction are explained under such a standard condition that a cleaning device in each embodiment is installed.

Figure 1:
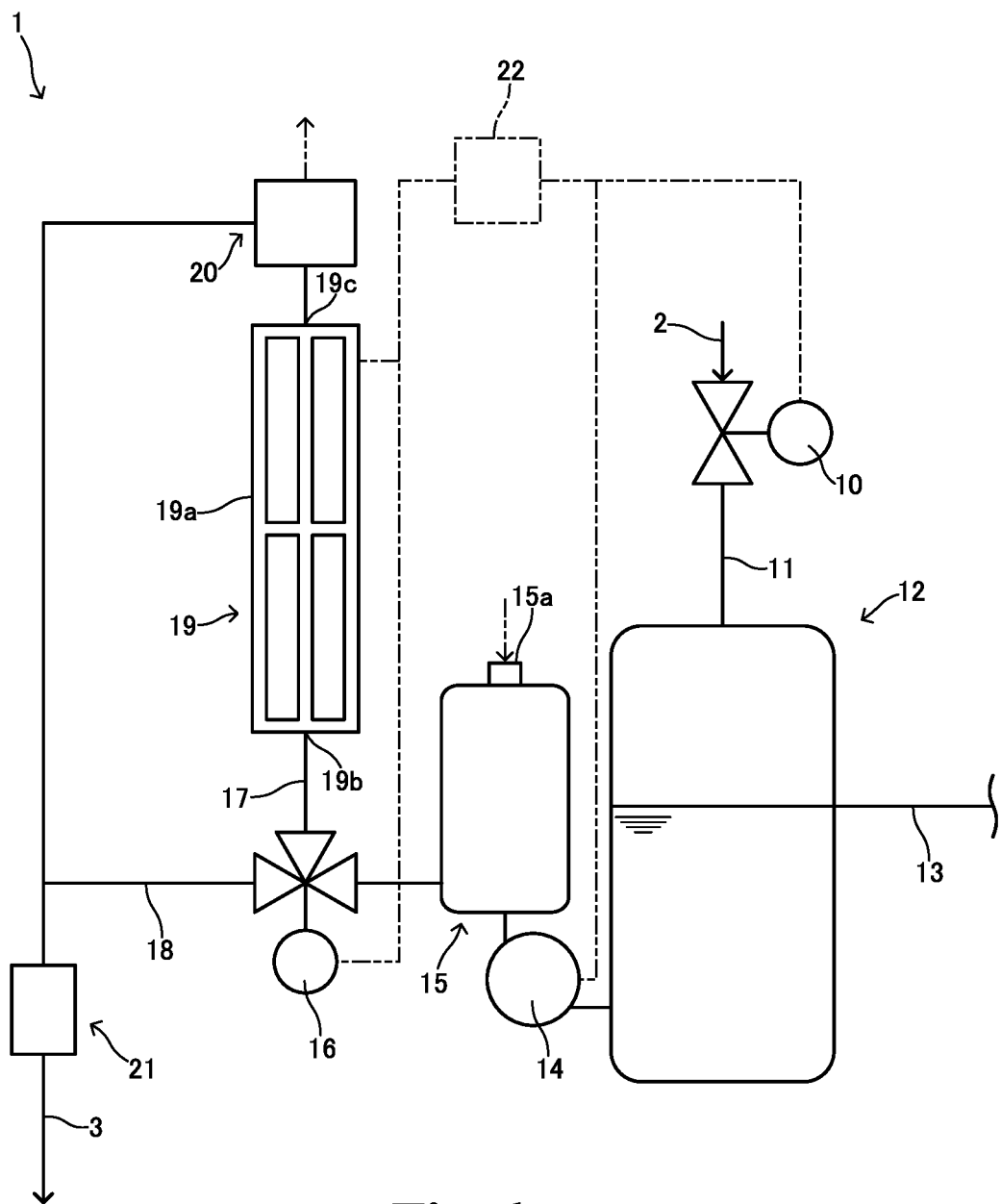
FIG. 1 is a schematic system configuration view diagrammatically illustrating one example of a cleaning device according to one embodiment of the present invention.
Figure 2:
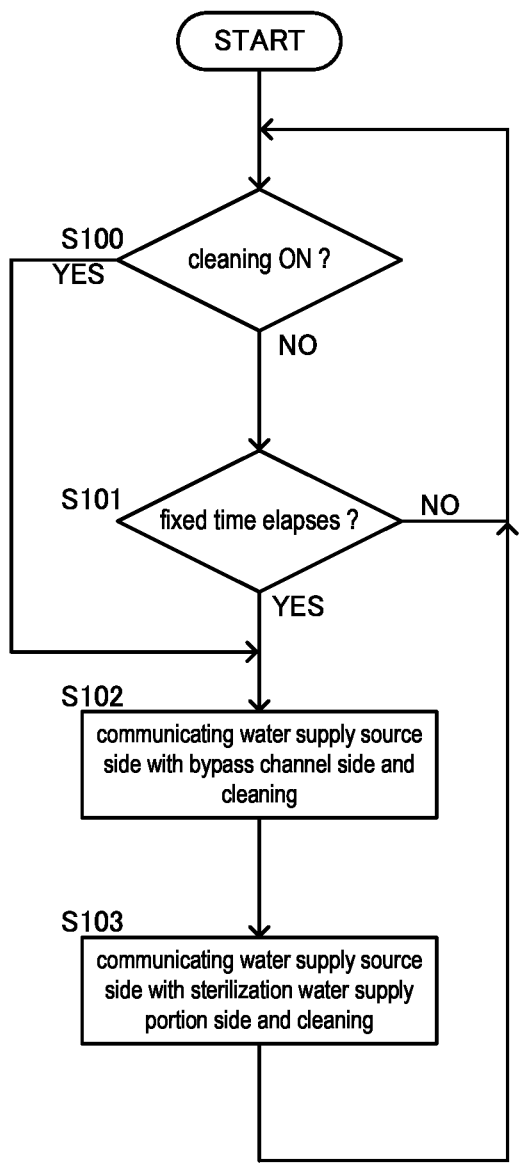
FIG. 2 is a schematic flow chart diagrammatically illustrating one example of a cleaning method executed by the cleaning device according to one embodiment of the present invention.

FIG. 1 and FIG. 2 diagrammatically illustrate one example of the cleaning device in the first embodiment and one example of a cleaning method which is executed using the cleaning device.

A cleaning device 1 in the embodiment has a disinfection water supply portion 19 to supply cleaning water with a dissolved disinfection component, and a bubble generation portion 21 provided on the downstream side of the disinfection water supply portion 19 to contain bubbles in cleaning water. In such a configuration, the disinfection component is contained in cleaning water itself, therefore the disinfection ability is improved. Compared with a configuration in which the bubble generation portion 21 is provided on the upstream side of the disinfection water supply portion 19, the disinfection water supply portion 19 is provided on the upstream side of the bubble generation portion 21, so that dissipation of bubbles is restrained and adverse effect caused by bubbles is also restrained depending on the configuration of the disinfection water supply portion 19. The bubble generation portion 21 is provided on the downstream side of the disinfection water supply portion 19, so that part of the disinfection component contained in cleaning water is vaporized to be made into bubbles or incorporated in bubbles. Thus, in addition to the so called direct disinfection effect of the cleaning water containing a disinfection component and dirt removing effect of bubbles, the disinfection component in the form of bubbles or incorporated into bubbles is gradually dissolved in cleaning water and the disinfection effect is prolonged.

In the embodiment, the cleaning device 1 has a gas dissolution portion 15 to dissolve gas into cleaning water on the upstream side of the disinfection water supply portion 19. In such a configuration, the gas dissolved in the gas dissolution portion 15 is made into bubbles in the bubble generation portion 21 and the bubbles are contained in cleaning water. Thus, compared with a configuration such that the gas dissolution portion 15 and a gas-liquid mixing portion are provided on the downstream side of the disinfection water supply portion 19, the disinfection component contained in cleaning water is restrained from being reduced by decomposition or the like. In addition to the gas dissolved in the gas dissolution portion 15, the disinfection component to be vaporized is effectively made into bubbles or is incorporated into the bubbles, thereby effectively prolonging the disinfection effect.

In the embodiment, a water storage portion 12 to temporarily store cleaning water and a pump 14 to send the cleaning water stored in the water storage portion 12 to the downstream side are provided on the upstream side of the disinfection water supply portion 19. In such a configuration, compared with a configuration in which a water pipe is directly connected to the disinfection water supply portion 19, the flow rate of the cleaning water supplied to the disinfection water supply portion 19 is kept constant and dispersion in the concentration of the disinfection component contained in cleaning water is reduced.

The water storage portion 12 is in the shape of a tank to store the cleaning water supplied through a water supply channel 11 connected to a water supply source 2. In the embodiment, the water storage portion 12 has an overflow channel 13 so as to form a water discharge port space between a water discharge port of the water supply channel 11 and a water surface, i.e., an overflow water surface. The figures exemplify one example that the overflow channel 13 is connected to a side wall portion of the water supply portion 12; however, the overflow channel 13 can be provided so as to rise vertically from the bottom side of the water storage portion 12 in the water storage portion 12. In place of a configuration having the water discharge port space to isolate the water supply source 2 side from the water storage portion 12, a vacuum breaker can be suitably provided.

The water supply channel 11 to supply cleaning water to the water storage portion 12 has a water supply valve 10 to supply or shut off cleaning water by opening or closing the water supply channel 11. The water supply valve 10 can be an electromagnetic valve or a level regulating valve, i.e., a so-called ball tap. The water supply source 2 can be waterworks or other water storage tanks. The figures exemplify that the water supply channel 11 is connected to a top wall portion defining the upper side of the water storage portion 12; however, the water supply channel 11 can be connected to the side wall portion of the upper end portion of the water storage portion 12. It can be configured such that the water supply valve 10 is opened when the storage level in the water storage portion 12 reaches a fixed lower limit. In such a case, the water supply portion 12 can be provided with a suitable level gauge, a float, i.e., a floating ball or the like, to open or close the water supply valve 10. Or the water supply valve 10 can be always open while the cleaning device 1 is operated.

The pump 14 is provided between the water storage portion 12 and the gas dissolution portion 15. The suction port of the pump 14 is connected to the discharge side of the water supply portion 12 through a pipeline and the exhaust port of the pump 14 is connected to the inlet port of the gas dissolution port 15 through a pipeline.

The gas dissolution portion 15 is in the shape of a tank and has the inlet port at the lower end portion, or the bottom wall portion, in the figure, to be connected to the pump 14. A gas-liquid mixing chamber to mix the cleaning water flown from the inlet port with gas, an intermediate chamber, and a gas-liquid separation chamber are provided in the gas dissolution portion 15; however those widely known chambers are omitted in the figures. The gas-liquid mixing chamber and the intermediate chamber are connected via a communication port provided for a separation wall which separates the chambers, the intermediate chamber and the gas-liquid separation chamber are connected via a communication port provided for a separation wall which separates the chambers. The figures exemplify that an outlet port is provided at the lower end portion of the side wall portion of the gas dissolution portion 15 on the downstream side of the gas-liquid separation chamber.

The gas dissolution portion 15 also has a gas intake portion 15a to take gas into the gas-liquid mixing chamber. Gas can be taken into the gas-liquid mixing chamber by a negative pressure action caused by operating the pump 14 in order to take in gas from a gas intake portion 15a. Or gas is unable to be taken in while the pump 14 is operating, and when the pump 14 is stopped, gas to be dissolved at the next operation can be taken in. In such a configuration, compared with the configuration in which the gas intake portion is provided on the suction side of the pump 14, the pump 14 is downsized. In case that the gas to be taken in is functional gas which is different from atmosphere or air, the amount of used functional gas is optimized. In such a configuration, a suitable bypass channel or the like can be provided so as to return the gas separated in the gas-liquid separation chamber to the gas-liquid mixing chamber.

In the gas dissolution pump 15, the pressurized cleaning water is introduced into the gas-liquid mixing chamber when the pump 14 is operated, although detailed explanation is omitted. In the gas-liquid mixing chamber, cleaning water and gas are mixed and stirred while colliding with the inner wall, and the gas is dissolved in the cleaning water under pressure and reaches the gas-liquid separation chamber through the intermediate chamber. Undissolved gas is separated in the gas-liquid separation chamber, the gas-dissolved cleaning water in which gas is dissolved is supplied to the downstream side from the outlet port of the gas dissolution portion 15. The gas dissolution portion 15 is not limited to the one configured as above. For example, the gas dissolution portion 15 can be provided with a discharge port to discharge the gas separated in the gas-liquid separation chamber, and several kinds of configurations are applicable.

In the disinfection water supply portion 19, a disinfection component is contained in the gas-dissolved cleaning water supplied from the gas dissolution portion 15 to be supplied to the downstream side. In the embodiment, the disinfection water supply portion 19 has an electrolytic cell 19a to generate cleaning water containing a disinfection component by electrolyzing the cleaning water from the water supply source 2 side. Namely, the disinfection water supply portion 19 is an electrolytic type. In such a configuration, compared with the configuration in which cleaning water containing a disinfection component is generated by dissolving a medicament, supplementation of a medicament or the like is not required and maintenability is improved.

In this embodiment, an outlet port 19c to flow out cleaning water from the electrolytic cell 19a to the downstream side is provided so as to be positioned on the upper side of an inlet port 19b to flow cleaning water into the electrolytic cell 19a. In such a configuration, cleaning water remains in the electrolytic cell 19a after the device is stopped, and cleaning water containing a disinfection component is generated soon at the next startup.

The disinfection water supply portion 19 is configured to generate ozone water by electrolyzing cleaning water.

The electrolytic cell 19a of the disinfection water supply portion 19 is in the long shape in the vertical direction. The figures exemplify that the electrolytic cell 19a has the inlet port 19b at the lower end portion and the outlet port 19c at the upper end portion. Although omitted in the figures because it is widely known, a pair of electrodes which are connected to an electric power source and constitute a positive electrode and a negative electrode, a diamond electrode or an ion exchange membrane provided between the pair of electrodes are provided in the electrolytic cell 19a. When the disinfection water supply portion 19 is driven and energized to the electrode, ozone gas is generated by electrolyzing the cleaning water introduced in the electrolytic cell 19a, and ozone water is generated by dissolving the ozone gas into water in the dissolving portion.

The ozone concentration of the cleaning water or the ozone water generated in the disinfection water supply portion 19 can be suitably set depending on the application of the cleaning device 1, the cleaning target 3, and the installation position, or in view of improving the disinfection performance and safety. The ozone density of the cleaning water generated in the disinfection water supply portion 19 can be equal to or larger than 0.05 mg/l in view of the disinfection performance, preferably equal to or larger than 0.15 mg/l, or equal to or less than 7.0 mg/l in view of safety. When the cleaning target 3 of the cleaning device 1 is a pipe or the like and the vaporized disinfection component or ozone gas does not leak outside, the ozone concentration can be larger than the above-mentioned maximum value.

The disinfection water supply portion 19 is not limited to the one that generates cleaning water containing a disinfection component by electrolyzing cleaning water from the water supply source 2 side, and can be a storage tank to generate or store the cleaning water with a dissolved medicament constituting a disinfection component. The cleaning water containing a disinfection component is not limited to ozone water and can be hypochlorous acid water, strongly acid water, sodium hypochlorite solution, or hydrogen peroxide water. The cleaning water containing a disinfection component is only required to have higher disinfection performance than tap water, and is not limited to the above-mentioned electrolyzed water or the cleaning water with low persistency, and can be cleaning water of alcohol type such as ethanol or other kinds of cleaning water.

In the embodiment, the bubble generation portion 21 is configured such that the gas contained in cleaning water is made into bubbles and the bubbles are contained in the cleaning water by depressurizing or releasing pressure of the cleaning water with dissolved gas in the gas dissolution portion 15 on the upstream side. In such a configuration, minute bubbles are effectively contained in cleaning water. The bubble generation portion 21 can be a pressure releasing portion in the shape of a venturi tube. The bubbles contained in the cleaning water passed through the bubble generation portion 21 can be bubbles of a millimeter order, a micrometer order, or a nanometer order, or the bubbles of those orders can be mixed. The bubble can a minute bubble of which diameter is equal to or less than 1 millimeter, preferably equal to or less than 500 micrometer, or more preferably equal to or less than 100 micrometer. In the embodiment, the bubble generation portion 21 also works as a resistance portion to increase pressure on the downstream side of the disinfection water supply portion 19. In such a configuration, vaporization of the disinfection component contained in cleaning water is restrained. The resistance portion can be provided on the downstream side of the disinfection water supply portion 19 separately from the bubble generation portion 21.

In the embodiment, a gas discharge portion 20 to discharge gas is provided on the upstream side of the bubble generation portion 21. In such a configuration, it is difficult for gas such as large bubbles to be introduced into the bubble generation portion 21 and it is restrained that bubbles are reduced by combining with the bubbles generated in the bubble generation portion 21. The bubble discharge portion 20 is provided on the downstream side of the disinfection water supply portion 19. The figures exemplify that the gas discharge portion 20 is provided so as to be positioned on the upper side of the electrolytic cell 19a of the disinfection water supply portion 19.

The gas discharge portion 20 can be provided with a discharge port which is opened or closed by a float moving vertically in a float chamber or by a valve body connected to the float. The gas discharge portion 20 can be configured to allow gas passage only to the discharge side.

In the embodiment, the cleaning device 1 has a bypass channel 18 which connects the upstream side of the disinfection water supply portion 19 and the upstream side of the bubble generation portion 21 on the downstream side of the disinfection water supply portion 19. The cleaning device 1 has a switching valve 16 to selectively communicate the water supply source 2 with the disinfection water supply portion 19 side or the bypass channel 18 side. In such a configuration, the bubble-containing cleaning water containing a disinfection component and the bubble-containing cleaning water not containing a disinfection component can be supplied selectively. The disinfection water supply portion 19 provided with the electrolytic cell 19a as mentioned above achieves long life, and the disinfection water supply portion 19 in which a medicament is dissolved reduces the amount of used medicament.

In the embodiment, the pipeline on the downstream side of the gas dissolution portion 15 is branched into a disinfection-side water supply channel 17 and the bypass channel 18, and a three-way switching valve is provided on the branched portion as a switching valve 16. In place of such a configuration, an on-off valve can be respectively provided for the disinfection-side water supply channel 17 and the bypass channel 18.

The cleaning device 1 has a control circuit such as CPU, i.e., Central Processing Unit, a memory unit constituted with several kinds of memories and so on, and a control unit 22 having a power source and so on. The control unit 22 is connected with the water supply valve 10, the pump 14, the switching valve 16, the disinfection water supply portion 19 or the like via signal lines. Each part of the cleaning device 1 is controlled by the control unit 22 and several kinds of cleaning methods or cleaning modes to be mentioned later are executed. The control unit 22 is not limited to the one dedicated to the cleaning device 1 and can be provided apart from the cleaning device 1.

The cleaning water generated in the cleaning device 1 is supplied to a suitable cleaning target 3. The cleaning target 3 is not limited to a toilet 5 or a discharge channel 9 of the toilet 5, referring to FIG. 3, to be mentioned in the second embodiment, and can be either one of a discharge channel and a water supply target such as a kitchen system, a washstand system, a bathroom, a washing machine, or a dish washer. The cleaning device 1 is not limited to a configuration to be incorporated into several kinds of water using systems and devices, the cleaning device 1 can be used alone, or the cleaning target 3 can be perishable food. A water storage portion to temporarily store the generated cleaning water can be provided on the downstream side of the bubble generation portion 21, and the cleaning water can be supplied from the water storage portion to the cleaning target 3 by opening a suitable valve. Such a configuration stabilizes the flow rate of the cleaning water to be supplied to the cleaning target 3.

Next, one example of a cleaning method to be executed using the cleaning device 1 of the embodiment is explained also referring to FIG. 2.

The cleaning method is constituted to supply cleaning water to the cleaning target 3 each time a predetermined fixed time elapses. In such a constitution, propagation of bacteria of the cleaning target 3 is restrained. The fixed time can be set depending on the kinds of bacteria to be disinfected, can be suitably set in view of achieving water saving or electric power saving, can be about 1 to 24 hours, or can be preferably about 2 to 8 hours. The fixed time can be reset and clocked each time cleaning is executed by a suitable clock portion provided for the control unit 22. Namely, it can be constituted that cleaning water is supplied to the cleaning target 3 when the fixed time elapses after executing the previous cleaning.

The cleaning method is constituted such that the water supply source 2 side is communicated with the bypass channel 18 side and cleaning water is supplied to the cleaning target 3 after passing through the bubble generation portion 21 when the cleaning target 3 is being cleaned. Then, the cleaning water passed through the disinfection water supply portion 19 and the bubble generation portion 21 by communicating the water supply source 2 side with the disinfection water supply portion 19 side is supplied to the cleaning target 3. In such a constitution, after the dirt of the cleaning target 3 is removed by the cleaning water which does not contain a disinfection component, namely after pre-cleaning, the cleaning target 3 is effectively disinfected by the cleaning water containing a disinfection component. As a result, long-life and power saving are achieved or cost reduction is achieved, although they depend on the configuration of the disinfection water supply portion 19.

In the embodiment, as illustrated in FIG. 2, when cleaning operation is turned on by operating a suitable cleaning operation portion (step 100), the pump 14 is activated, cleaning water is supplied to the cleaning target 3 by communicating the water supply 2 side with the bypass channel 18 side, and cleaning or pre-cleaning is executed (step 102). Namely, the switching valve 16 is switched so as to communicate the downstream side of the gas dissolution portion 15 with the bypass channel 18. The pre-cleaning can be executed until a predetermined fixed pre-cleaning time elapses. The disinfection water supply portion 19 can be operated during the pre-cleaning. In such a constitution, cleaning water containing a disinfection component is generated in the disinfection water supply portion 19 during pre-cleaning. The cleaning operation portion can be an operation lever, an operation button, or the like, and can be constituted such that several kinds of sensors such as a human body detection sensor or a seating sensor can be operated as the cleaning operation, namely detection is operated as the cleaning operation.

After pre-cleaning is finished, cleaning water is supplied to the cleaning target 3 by communicating the water supply source 2 side with the disinfection water supply portion 19 side, and cleaning or disinfection cleaning is executed (step 103). Namely, the switching valve 16 is switched to communicate the downstream side of the gas dissolution portion 15 with the disinfection-side water supply channel 17. The disinfection cleaning can be executed until a predetermined fixed disinfection cleaning time elapses.

On the other hand, when the fixed time elapses without turning on cleaning or cleaning operation (step 100, step 101), the timer is reset and the disinfection cleaning is executed after the pre-cleaning as mentioned above (step 102, step 103).

It can be constituted such that cleaning is executed when cleaning operation is executed without elapsing the fixed time after the previous cleaning, and cleaning is executed when the fixed time elapses after the previous cleaning. In place of such a constitution, cleaning can be executed periodically or each time the fixed time elapses regardless of the cleaning operation. Namely, the fixed time can be measured without resetting the timer when cleaning operation is executed. The cleaning method using the cleaning device 1 is not limited to the above-mentioned embodiment. For example, the step 100, namely a step to determine whether cleaning operation is executed or not, can be omitted when the cleaning operation portion is not provided, and several kinds of embodiments are applicable.

Next, other embodiment is explained referring to the drawings.

In the following embodiment and variation, the difference from the embodiment explained above is mainly explained, the similar configurations are allotted with the same reference numerals and their explanations are omitted or briefly explained.

Figure 3:
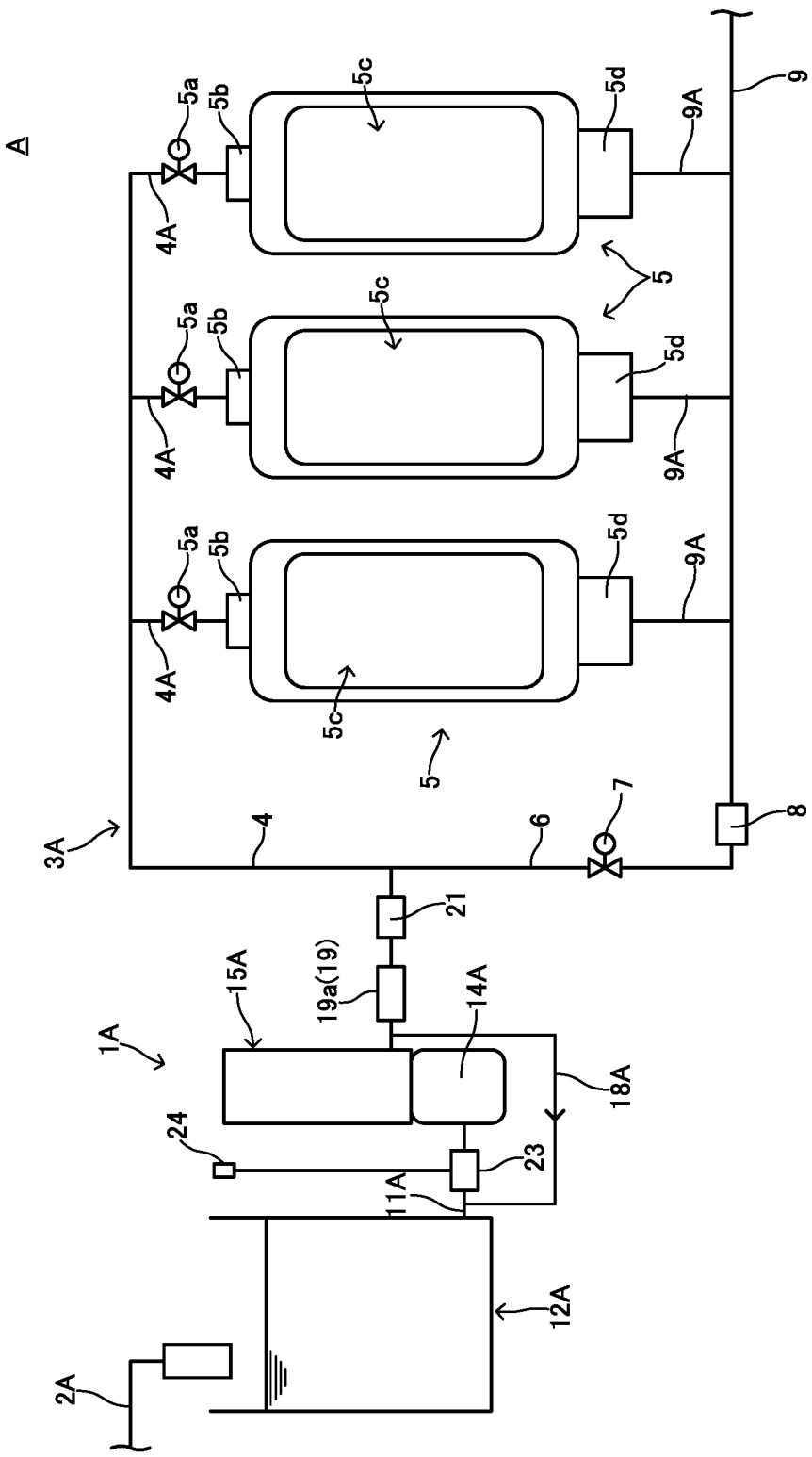
FIG. 3 is a schematic system configuration view diagrammatically illustrating one example of a cleaning system according to one embodiment of the present invention provided with one example of a cleaning device according to another embodiment of the present invention.

FIG. 3 diagrammatically illustrates an example of a cleaning device according to the second embodiment and a cleaning system provided with the cleaning device.

A cleaning system A in the embodiment has a cleaning device 1A in the embodiment and the downstream side of the bubble generation portion 21 is connected to at least one of the water supply channel 4 to supply cleaning water to the toilet 5 and the water discharge channel 9 connected to the water discharge portion 5d of the toilet 5. In the embodiment, a cleaning target 3A is at least one of the toilet 5 and the water discharge channel 9. In such a configuration, both of or one of the water supply channel 4 and the water discharge channel 9 which is connected with the cleaning device 1A is effectively disinfected and cleaned by the cleaning water containing a disinfection component and the bubbles generated in the cleaning device 1A. Dirt such as urinary stones, i.e., calcium ion or germ, attached to the inside of at least one of the toilet 5 and the water discharge channel 9 is effectively removed by being absorbed in the bubbles contained in cleaning water, and accumulation of urinary stones is effectively restrained.

In the embodiment, the downstream side of the bubble generation portion 21 is connected to both of the water supply channel 4 and the water discharge channel 9. In the figures, a bypass water supply channel 6 branched from the water supply channel 4 on the downstream side of the bubble generation portion 21 is connected to the water discharge channel 9.

The embodiment exemplifies that the toilet 5 is a urinal to be used in a standing condition. The toilet 5 has a bowl portion, i.e., a pot-like portion, 5c, a water supply portion 5b connected to the water supply channel 4, and a water discharge portion 5d to discharge urine and cleaning water.

The water supply portion 5b has an exhaust portion such as a spreader to exhaust cleaning water along the inner surface of the bowl portion 5c.

The discharge portion 5d constitutes a trap portion in the shape of a bell trap or a P-trap and is connected to the discharge channel 9. The toilet 5 can be an elongated floor-type urinal to be provided on the floor or a wall-type urinal to be hooked on the wall surface. The cleaning system A in the embodiment can be constituted as a toilet cleaning system including the toilet 5.

In the embodiment, the water supply channel 4 is branched into plural pipes, three pipes in the figure, and supplies cleaning water to a plurality of toilets 5, 5, 5. Branch pipelines 4A, 4A, 4A of the water supply channel 4 are respectively connected to water supply portions Sb, Sb, Sb of the toilets 5, 5, 5. The branch pipelines 4A, 4A, 4A respectively have water supply valves 5a, 5a, 5a to supply or shut off cleaning water by opening or closing operation. The discharge portions 5d, 5d, 5d of the toilets 5, 5, 5 are respectively connected with water discharge pipelines 9A, 9A, 9A connected to the discharge channel 9 in the shape of horizontal piping.

The end portion on the downstream side of the bypass water supply channel 6 is connected to a connection portion of the water discharge channel 9 and the water discharge pipeline 9A connected to the toilet 5 on the most upstream side of the water discharge channel 9 in the water discharge direction. Namely, the end portion on the downstream side of the bypass water supply channel 6 is connected to the end portion on the upstream side of the region provided so as to extend in the approximately horizontal direction of the water discharge channel 9.

The bypass water supply channel 6 has a bypass valve 7 to supply or shut off cleaning water by opening or closing the bypass water supply channel 6. The bypass water supply channel 6 has a backflow prevention portion 8 such as a back-flow prevention valve, i.e., a non-return valve or a check valve, to prevent backflow into the upstream side. The backflow prevention portion 8 is provided on the downstream side, or on the discharge channel 9 side, of the bypass valve 7.

The cleaning device 1A has a water storage portion 12A, which is substantially in the same manner as the one mentioned above, to temporarily store the cleaning water from a water supply source 2A side. The figures exemplify that the above-mentioned water supply valve is not provided for the water supply channel constituting the water supply source 2A; however, the embodiment is not limited to such an exemplification. In the exemplification, the water storage portion 12A is formed like a tank of which upper portion without a top wall portion is open; however, the embodiment is not limited to such an exemplification. Although it is not illustrated in the figures, the overflow channel as mentioned above can be provided. The water storage portion 12A has a suitable level gauge so as to store cleaning water at a fixed level.

A water supply channel 11A between the water storage portion 12A and a pump 14A on the downstream side of the water storage portion 12A has an ejector portion 23 to take in gas through a gas intake portion 24. The gas intake portion 24 can be open to atmosphere at the tip end of the pipeline or can be provided with an on-off valve in the midway of the pipeline. The gas intake portion 24 is connected to a nozzle portion of the ejector portion 23. A flow rate adjusting portion capable of adjusting the flow rate of gas supplied to the ejector portion 23 can be provided in the midway of the pipeline of the gas intake portion 24.

The ejector portion 23 is configured to take in gas through the gas intake portion 24 by the ejector effect of the negative pressure action of the cleaning water passing through the nozzle portion. The gas taken in by the ejector portion 23 is introduced into the gas dissolution portion 15A by the pump 14A and is dissolved into cleaning water in substantially the same manner as mentioned above.

Also in the embodiment, the disinfection water supply portion 19 and the bubble generation portion 21 are provided on the downstream side of the gas dissolution portion 15A. In the figure, the disinfection water supply portion 19 is laterally long; however, it can be vertically long as mentioned above.

In the embodiment, a recirculation channel 18A is provided so as to connect the water supply channel 11A between the gas dissolution portion 15A and the disinfection water supply portion 19 with the water supply channel 11A on the upstream side of the ejector portion 23.

In such a configuration, part of the cleaning water passed through the gas dissolution portion 15A is returned to the upstream side, and the flow rate of the cleaning water supplied to the disinfection water supply portion 19 is stabilized.

It is not illustrated in the figures, the embodiment is also provided with the control unit 22, referring to FIG. 1, which is connected to each part of the cleaning system A for controlling.

In the cleaning system A as configured above, the pump 14A is operated with the bypass valve 7 closed, the water supply valve 5a of the toilet 5 is opened after cleaning operation, cleaning water containing a disinfection component and bubbles is supplied to the bowl portion 5c of the toilet 5 after cleaning operation. Substantially in the same manner as mentioned above, when the cleaning operation portion provided for the toilet 5 is operated or the human body detection sensor detects access or separation of a human body, it is determined that cleaning operation is executed, and such a toilet cleaning mode can be executed.

When the pump 14A is operated and the bypass valve 7 is opened, cleaning water containing a disinfection component and bubbles is directly supplied to the water discharge channel 9 through the bypass water supply channel 6. When the pump 14A is operated and the bypass valve 7 is opened with all the water supply valves 5a, 5a, 5a closed, cleaning water containing a disinfection component and bubbles can be supplied only to the bypass water supply channel 6 side.

When cleaning operation is executed for example, after executing a toilet cleaning mode in which cleaning water is supplied to the bowl portion 5c of the toilet 5, a water discharge channel cleaning mode can be executed such that cleaning water is supplied to the water discharge channel 9 through the bypass water supply channel 6.

As mentioned in the first embodiment, both or one of the toilet cleaning mode and the water discharge channel cleaning mode can be executed each time the fixed time elapses, namely on a regular basis.

In the embodiment, cleaning water containing a disinfection component and bubbles is simultaneously supplied to both of the bowl portion 5c of at least one toilet 5 and the bypass water supply channel 6. Compared with the configuration that cleaning water is selectively supplied to the toilet 5 or the bypass water supply channel 6, both of the bowl portion 5c of the toilet 5 and the water discharge channel 9 are effectively cleaned.

Figure 4:
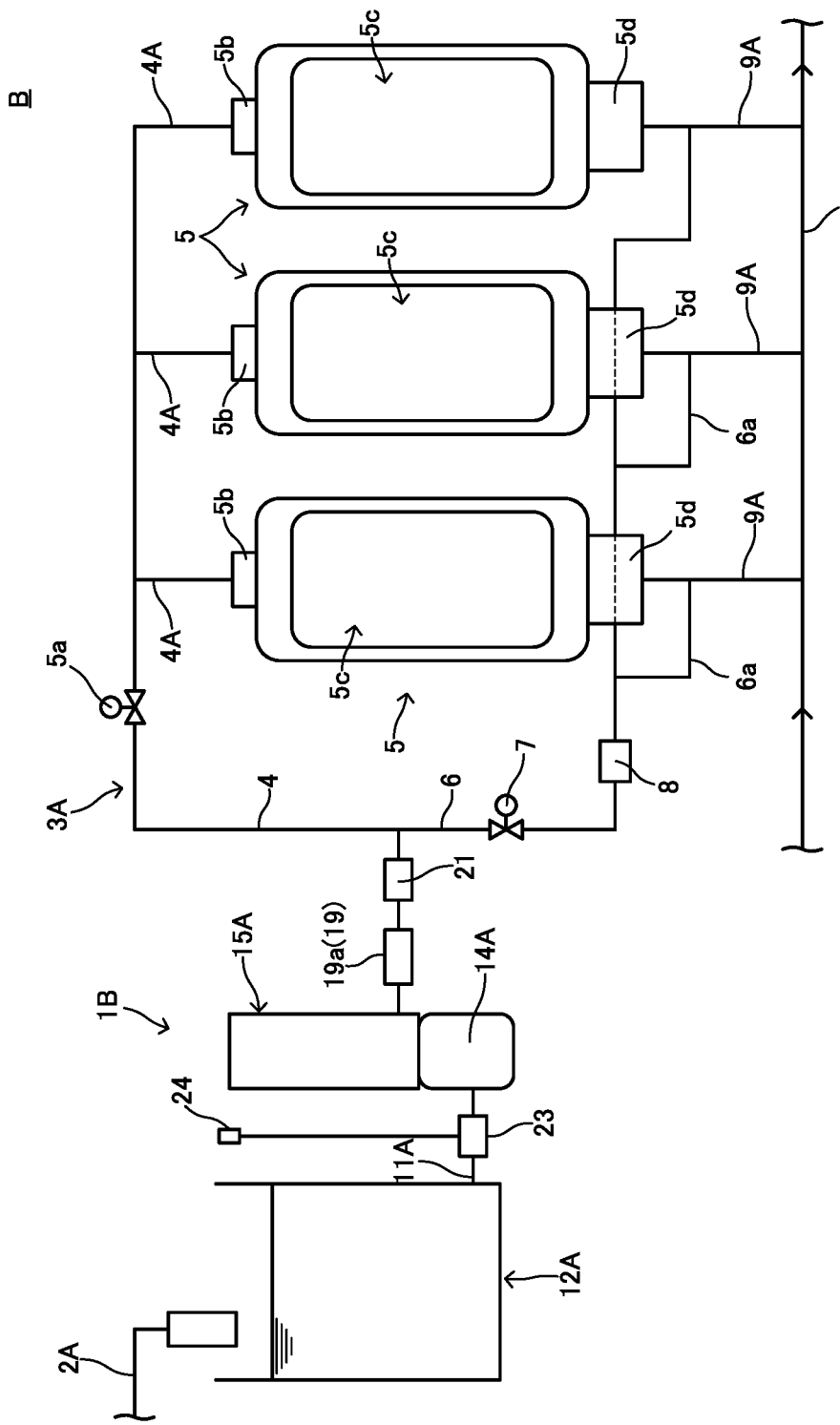
FIG. 4 is a schematic system configuration view diagrammatically illustrating one variation of the cleaning system provided with one variation of the cleaning device.
Figure 5:
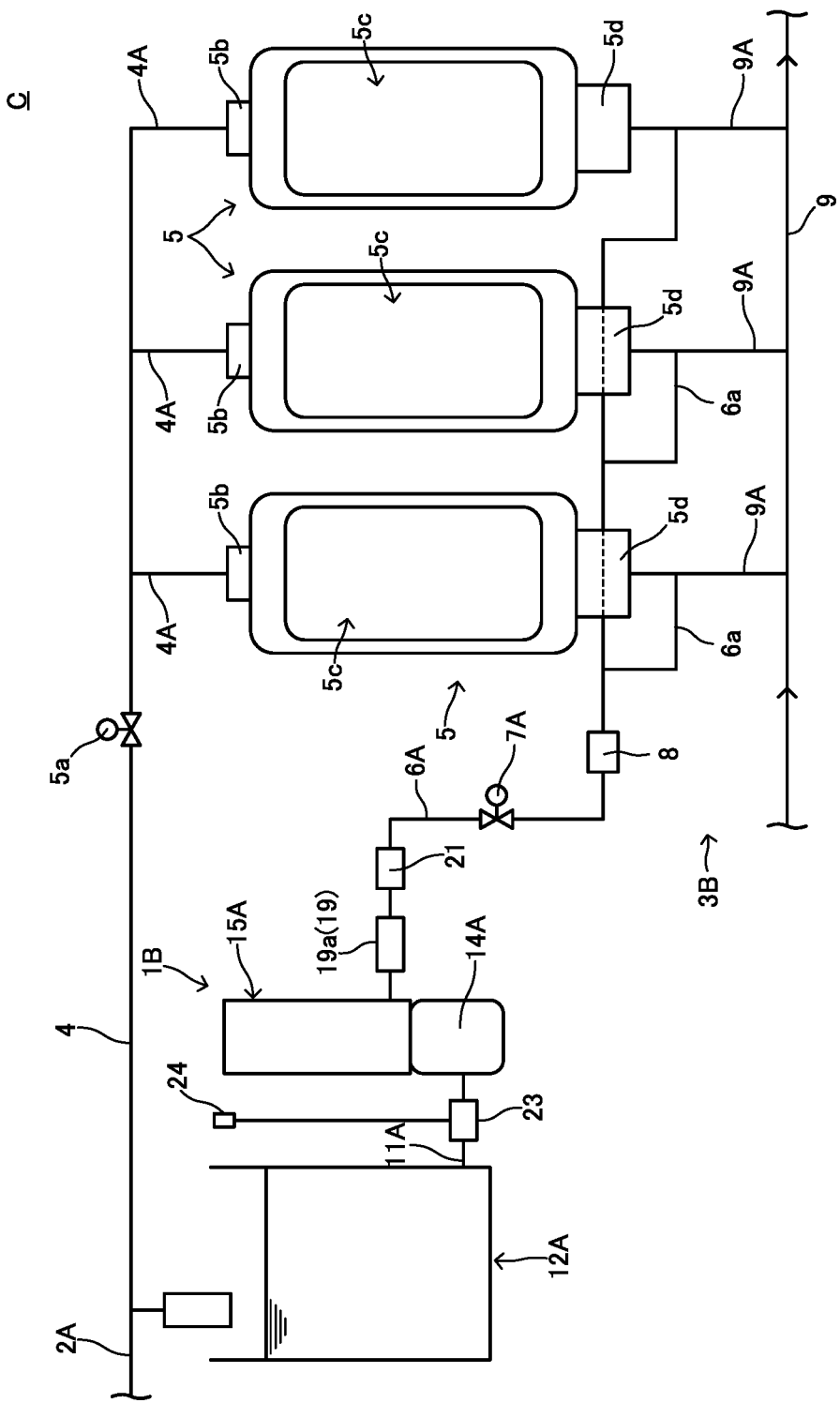
FIG. 5 is a schematic system configuration view diagrammatically illustrating one variation of the cleaning system provided with one variation of the cleaning device.

FIG. 4 and FIG. 5 diagrammatically illustrate one variation of the cleaning device and the cleaning system in the second embodiment.

In the first variation in FIG. 4, a cleaning device 1B is similar to the above-mentioned embodiment excluding that the recirculation channel 18A is provided.

In a cleaning system 1B in the first variation, the water supply valve 5a is provided on the upstream side region of the water supply channel 4, not for the branch pipelines 4A, 4A, 4A connected to the water supply portions Sb, Sb, 5b of the toilets 5, 5, 5. The water supply valve 5a is provided so as to be positioned on the upstream side of the by branch pipeline 4A connected to the toilet 5 on the most upstream side of the water supply channel 4 in the water supply direction. In such a configuration, when one water supply valve 5a is opened, cleaning water is simultaneously supplied to the toilets 5, 5,5.

In the cleaning system B, in place of such a configuration that the bypass water supply channel 6 is connected to the end portion on the upstream side of the water discharge channel 9 in the shape of horizontal piping, the bypass water supply channel 6 is connected to the water discharge pipelines 9A, 9A, 9A connected to the water discharge portions 5d, 5d, 5d of the toilets 5, 5, 5. In such a configuration, the water discharge pipelines 9A, 9A, 9A of the toilets 5, 5, 5 are effectively cleaned. The figures exemplify that the bypass water supply channel 6 is connected to the middle region of the water discharge pipelines 9A, 9A, 9A; however, the bypass water supply channel 6 can be connected to the end portion on the upstream side of the water discharge pipelines 9A, 9A, 9A, and can be connected to the water discharge portions 5d, 5d, 5d. In such a configuration, the discharge portions 5d, 5d, 5d are also effectively cleaned. The figures exemplify that the branch pipelines 6a, 6a branched from the bypass water supply channel 6 is connected to the water discharge pipelines 9A, 9A on the upstream side of the water discharge pipeline 9A connected with the end portion of the bypass water supply channel 6 on the downstream side.

In the second variation in FIG. 5, a cleaning target 3B of a cleaning system C is the water discharge channel 9 as one of the toilet 5 and the water discharge channel 9. In the variation, the water supply channel 4 to supply cleaning water to the toilets 5, 5, 5 is connected to the water supply source 2A, not to the water supply channel 11A of the cleaning device 1B. One water supply valve 5a is provided on the upstream side region of the water supply channel 4 like the first variation.

A downstream-side water supply channel 6A of the bubble generation portion 21 of the cleaning device 1B is connected to the water discharge pipelines 9A, 9A, 9A connected to the discharge portions 5d, 5d, 5d of the toilets 5, 5, 5 like the first variation. A downstream-side water supply channel 6A has a cleaning water supply valve 7A similar to the above-mentioned bypass valve 7. In this variation, like the first variation, the water discharge pipelines 9A, 9A, 9A of the toilets 5, 5, 5 are effectively cleaned.

In the second embodiment and each variation, the bypass channel 18 and the switching valve 16 can be provided like the first embodiment. In such a case, disinfection cleaning can be executed after pre-cleaning in both or one of the toilet cleaning mode and the water discharge channel cleaning mode like the first embodiment.

In the second embodiment and each variation, the gas discharge portion 20 as mentioned in the first embodiment can be provided. Some of the different configurations as explained in each embodiment and each variation can be rearranged or combined to be practically used.

For example, the cleaning device 1 explained in the first embodiment can be used as the cleaning device of the cleaning systems A, B, C in the second embodiment and each variation, and several rearrangements or combinations are applicable.

In the second embodiment and the first variation, although the cleaning target 3A is a plurality of toilets 5, 5, 5, it can be one toilet 5, and it is not limited to a urinal and can be a squat type or a seat type toilet stool. The cleaning targets 3A, 3B of the cleaning devices 1A, 1B in the second embodiment and each variation are not limited to the toilet 5 or the water discharge channel 9 of the toilet 5, and can be several objects to be cleaned as mentioned above.

In each embodiment and each variation, the water storage portions 12, 12A and the pumps 14, 14A are provided; however, a water pipe can be directly connected as the water supply pipe to the gas dissolution portions 15, 15A.

In each embodiment and each variation, the bubble generation portion 21 is configured to contain bubbles in cleaning water by depressurizing or releasing pressure of the cleaning water dissolved with gas in the gas dissolution portions 15, 15A on the upstream side; however, the embodiment and variation are not limited to such a configuration. For example, bubbles can be contained by heating cleaning water. A gas intake channel can be connected to the gas-liquid mixing portion in the shape of a venturi pipe, the gas taken in to be mixed with cleaning water by ejector effect can be sheared and subdivided by sudden change in pressure while passing through a throttling portion, and can be mixed in cleaning water in the form of minute bubbles. Each configuration of the cleaning devices 1, 1A, 1B in the above-mentioned embodiments and variations is only one example and several variations are applicable.

REFERENCE SIGNS LIST

A, B, C cleaning system
1, 1A, 1B cleaning device
2, 2A water supply source
3, 3A, 3B cleaning target
4 water supply channel
5 toilet
5d water discharge portion
9 water discharge channel
12, 12A water storage portion
14, 14A pump
15, 15A gas dissolution portion
16 switching valve
18 bypass channel
19 disinfection water supply portion
19a electrolytic cell
19b inlet port
19c outlet port
20 gas discharge portion
21 bubble generation portion

The invention claimed is:
1. A cleaning device comprising:
a disinfection water supplier that supplies cleaning water with a dissolved disinfection component;
a bubble generator to contain bubbles into the cleaning water on a downstream side of the disinfection water supplier, wherein an inlet of the bubble generator is communicatively connected to an outlet port of the disinfection water supplier;
a bypass channel to connect an upstream side of the disinfection water supplier with an upstream side of the bubble generator on a downstream side of the disinfection water supplier; and
a switching valve to selectively communicate a water supply source side with a disinfection supplier side or a bypass channel side, the switching valve being provided at an upstream side of the disinfection water supplier.

2. The cleaning device according to claim 1,
wherein the cleaning device comprises a gas dissolver that dissolves gas into the cleaning water on an upstream side of the disinfection water supplier, wherein the gas dissolver has an outlet communicatively connected to an inlet port of the disinfection water supplier.

3. The cleaning device according to claim 2,
wherein on an upstream side of the disinfection water supplier, the cleaning device comprises a water storage to temporarily store cleaning water and a pump to send cleaning water stored in the water storage to a downstream side.

4. The cleaning device according to claim 2,
wherein the disinfection water supplier comprises an electrolytic cell to electrolyze cleaning water supplied from a water supply source side and to generate cleaning water containing a disinfection component, and the outlet port that flows out cleaning water from the electrolytic cell to a downstream side is positioned on an upper side of the inlet port that flows cleaning water into the electrolytic cell.

5. The cleaning device according to claim 4,
wherein on an upstream side of the disinfection water supplier, the cleaning device comprises a water storage to temporarily store cleaning water and a pump to send cleaning water stored in the water storage to a downstream side.

6. The cleaning device according to claim 1,
wherein the disinfection water supplier comprises an electrolytic cell to electrolyze cleaning water supplied from a water supply source side and to generate cleaning water containing a disinfection component, and the outlet port that flows out cleaning water from the electrolytic cell to a downstream side is positioned on an upper side of an inlet port that flows cleaning water into the electrolytic cell.

7. The cleaning device according to claim 6,
wherein on an upstream side of the disinfection water supplier, the cleaning device comprises a water storage to temporarily store cleaning water and a pump to send cleaning water stored in the water storage to a downstream side.

8. The cleaning device according to claim 1,
wherein the cleaning device comprises a gas dissolver that dissolves gas into the cleaning water on an upstream side of the disinfection water supplier, the gas dissolver having a gas-liquid mixing chamber to mix and stir pressurized cleaning water and gas, and
wherein the disinfection water supplier comprises an electrolytic cell to electrolyze cleaning water supplied from a water supply source side and to generate cleaning water containing a disinfection component, and the outlet port that flows out cleaning water from the electrolytic cell to a downstream side is positioned on an upstream side of an inlet port that flows cleaning water into the electrolytic cell.

9. The cleaning device according to claim 8,
wherein on an upstream side of the disinfection water supplier, the cleaning device comprises a water storage to temporarily store cleaning water and a pump to send cleaning water stored in the water storage to a downstream side.

10. The cleaning device according to claim 1,
wherein the cleaning device comprises a gas discharger that discharges gas on an upstream side of the bubble generator.

11. The cleaning device according to claim 10,
wherein on an upstream side of the disinfection water supplier, the cleaning device comprises a water storage to temporarily store cleaning water and a pump to send cleaning water stored in the water storage to a downstream side.

12. The cleaning device according to claim 1,
wherein on an upstream side of the disinfection water supplier, the cleaning device comprises a water storage to temporarily store cleaning water and a pump to send cleaning water stored in the water storage to a downstream side.

13. A cleaning system comprising the cleaning device according to claim 1,
wherein a downstream side of the bubble generator is connected to at least one of a water supply channel to supply cleaning water to a toilet and a water discharge channel connected to a water discharger of the toilet.

14. A cleaning method for cleaning a cleaning target using the cleaning device according to claim 1,
wherein cleaning water is supplied to the cleaning target each time a predetermined fixed time elapses.

15. A cleaning method for cleaning a cleaning target using the cleaning device according to claim 1,
wherein for cleaning the cleaning target, cleaning water passed through the bubble generator by communicating the water supply source side with the bypass channel side is supplied to the cleaning target, then cleaning water passed through the disinfection water supplier and the bubble generator by communicating the water supply source side with the disinfection water supplier side is supplied to the cleaning target.

16. The cleaning device according to claim 1,
wherein the cleaning device comprises a gas dissolver that dissolves gas into the cleaning water on an upstream side of the disinfection water supplier, and
wherein the gas dissolver has a gas-liquid mixing chamber to mix and stir pressurized cleaning water and gas.

17. The cleaning device according to claim 16,
wherein on an upstream side of the disinfection water supplier, the cleaning device comprises a water storage to temporarily store cleaning water and a pump to send cleaning water stored in the water storage to a downstream side.

18. A cleaning method for cleaning a cleaning target using the cleaning device according to claim 16,
wherein for cleaning the cleaning target, cleaning water passed through the bubble generator by communicating the water supply source side with the bypass channel side is supplied to the cleaning target, then cleaning water passed through the disinfection water supplier and the bubble generator by communicating the water supply source side with the disinfection water supplier side is supplied to the cleaning target.

* * * * *